United States Patent
Iwasaki (10) Patent No.: US 8,000,444 B2
(45) Date of Patent: Aug. 16, 2011

(54) VERTICAL/HORIZONTAL SMALL ANGLE X-RAY SCATTERING APPARATUS AND METHOD FOR MEASURING SMALL ANGLE X-RAY SCATTERING

(75) Inventor: Yoshio Iwasaki, Akiruno (JP)

(73) Assignee: Rigaku Corporation, Tokyo (JP)

( * ) Notice: Subject to any disclaimer, the term of this patent is extended or adjusted under 35 U.S.C. 154(b) by 207 days.

(21) Appl. No.: 12/064,990

(22) PCT Filed: Jul. 4, 2006

(86) PCT No.: PCT/JP2006/313299
§ 371 (c)(1),
(2), (4) Date: May 1, 2009

(87) PCT Pub. No.: WO2007/026461
PCT Pub. Date: Mar. 8, 2007

(65) Prior Publication Data
US 2009/0213992 A1 Aug. 27, 2009

(30) Foreign Application Priority Data
Aug. 29, 2005 (JP) .................................. 2005-247473

(51) Int. Cl.
*G01N 23/201* (2006.01)
*G01N 23/20* (2006.01)
(52) U.S. Cl. ................ 378/88; 378/71; 378/79; 378/81; 378/86
(58) Field of Classification Search .................... 378/70, 378/71, 73, 79, 80, 86, 88, 89, 90
See application file for complete search history.

(56) References Cited

U.S. PATENT DOCUMENTS
6,041,098 A * 3/2000 Touryanski et al. ............ 378/70
(Continued)

FOREIGN PATENT DOCUMENTS
JP 02-085747 3/1990
(Continued)

OTHER PUBLICATIONS

"Characterization of Polymer Thin Films With Small-Angle X-ray Scattering under Grazing Incidence (GISAXS)", Smilgies et al, Synchrotron Radiation News, vol. 15, No. 5, 2002 pp. 35-42.
(Continued)

*Primary Examiner* — Allen C. Ho
(74) *Attorney, Agent, or Firm* — Antonelli, Terry, Stout & Kraus, LLP.

(57) ABSTRACT

A vertical/horizontal small angle X-ray scattering apparatus, for enabling plural numbers of X-ray diffraction measurements, such as, transmission small angle X-ray diffraction, reflection small angle scattered X-ray diffraction, and in-plane X-ray diffraction, etc., comprises an X-ray generating apparatus 11 for generating X-ray, an optic system 16 for forming the X-ray into a predetermined incident beam of X-ray, a sample holder portion 120 for mounting a sample to be measured thereon, to irradiate the incident beam of X-ray thereupon, a vacuum path 17 for passing through small angle scattered X-ray from the sample, and an X-ray detector 18 for detecting the small angle scattered X-ray passing through the vacuum path, wherein the sample holder portion is fixed on a support base 110, while attaching the X-ray generating apparatus, the optic system, the vacuum path and the X-ray detector on a bench 100, as well, to be rotatable around the sample holder portion, and thereby enabling plural numbers of measurements of small angle X-ray scattering.

6 Claims, 11 Drawing Sheets

U.S. PATENT DOCUMENTS

| | | | | |
|---|---|---|---|---|
| 6,226,349 B1 * | 5/2001 | Schuster et al. | | 378/84 |
| 6,330,301 B1 * | 12/2001 | Jiang | | 378/85 |
| 6,718,008 B1 * | 4/2004 | He et al. | | 378/71 |
| 6,731,719 B2 * | 5/2004 | Fewster et al. | | 378/71 |
| 6,895,075 B2 * | 5/2005 | Yokhin et al. | | 378/90 |
| 6,937,695 B2 * | 8/2005 | Hoshino | | 378/86 |
| 6,956,928 B2 * | 10/2005 | He et al. | | 378/87 |
| 6,993,113 B2 * | 1/2006 | Hoshino et al. | | 378/86 |
| 7,145,983 B2 * | 12/2006 | Taguchi et al. | | 378/71 |
| 7,258,485 B2 * | 8/2007 | Nakano et al. | | 378/205 |
| 7,269,245 B2 * | 9/2007 | He et al. | | 378/71 |
| 7,443,952 B2 * | 10/2008 | Dosho et al. | | 378/71 |
| 7,471,766 B2 * | 12/2008 | Dosho | | 378/71 |
| 7,646,849 B2 * | 1/2010 | Iwasaki et al. | | 378/86 |
| 2004/0223586 A1 | 11/2004 | He et al. | | |

FOREIGN PATENT DOCUMENTS

| | | |
|---|---|---|
| JP | 07-140096 | 6/1995 |
| JP | 07-311163 | 11/1995 |
| JP | 10-300693 | 11/1998 |
| JP | 2000-146870 | 5/2000 |
| JP | 2000-266696 | 9/2000 |
| JP | 2000-325336 A1 | 11/2000 |
| JP | 2002-505903 A1 | 2/2002 |
| JP | 2004-020397 | 1/2004 |
| JP | 2004-177248 | 6/2004 |

OTHER PUBLICATIONS

Japanese Office Action, dated Aug. 2, 2010, issued in corresponding Japanese Patent Application No. 2007-533127.

* cited by examiner

VERTICAL/HORIZONTAL SMALL ANGLE X-RAY SCATTERING APPARATUS AND METHOD FOR MEASURING SMALL ANGLE X-RAY SCATTERING

FIELD OF THE INVENTION

The present invention relates to a small angle X-ray scattering apparatus for analyzing/estimating various kinds of material structures with using the small angle scattering of the X-ray, and in particular, it relates to a vertical/horizontal small angle X-ray scattering apparatus for enabling to change an incident angle of the X-ray into vertical or horizontal direction, depending upon a sample to be measured, and further it relates to a method for measuring the small angle X-ray scattering for a thin film-like sample.

BACKGROUND OF THE INVENTION

In recent years, an analysis/estimation upon the material structures with applying the X-ray therein, not limited to the conventional wide angle X-ray diffraction upon the crystalline structures, comes to be utilized, widely, for example, soft materials and biomaterials, including liquid samples therein, and further thin film-like material, etc., and in that case, there are many cases of using a small angle X-ray scattering apparatus for measuring the small angle X-ray scattering.

In general, for such the small angle X-ray scattering apparatus, it is common to adopt or employ, so-called the vertical structure, i.e., disposing an X-ray source, a slit or a pin-hole, a sample, a vacuum X-ray path, a two-dimensional X-ray detector, etc., in the horizontal direction, and for example, in the following Patent Document 1 is already known that having such the vertical structures, in relation to the small angle X-ray scattering apparatus, targeting the liquid samples or the like. Thus, the X-ray in the vertical direction from the X-ray source, which is provided on a bottom portion of the apparatus, irradiates upon the sample disposed in the horizontal direction, perpendicularly (at the right angle), after passing through the vacuum X-ray path disposed in an upper portion of that sample, reaches to the two-dimensional X-ray detector to be detected.

Further, though differing from such small angle X-ray scattering apparatus, but for example, in the following Patent Document 2 is already known an apparatus for analyzing/estimating the crystalline structures of proteins, wherein a large number of crystallization plates are formed within a sample holder, which is made up with a X-ray permeable material, and X-ray is irradiated from above or below upon the crystal of the proteins produced within those crystallization plates, and thereby to detect the X-ray diffracted thereon. By the way, within such the crystal estimation apparatus as already known by this Patent Document 1 is adapted such structures for rotating the X-ray irradiation means and the X-ray detection means thereof with respect to the sample holder, so as to obtain an integrated intensity of the X-ray diffracted upon the crystalline sample, but without rotating that sample holder, i.e., to obtain peak intensities from plural numbers of cross-sections, with respect to the X-rays reflected upon the crystals of the protein distributing in a spherical manner.

And, but also different from the small angle X-ray scattering apparatus, for example, in the following Patent Document 3 is already known the Lang's camera, wherein an X-ray source, a sample (e.g., a large-sized single-crystal wafer), and an X-ray exposure body (i.e., a fluorescent plate) are disposed, sequentially, from an upper position, into the vertical direction, for the purpose of achieving easy loading/unloading of the large-sized single-crystal wafer, as a measuring object, and also easy setting job thereof, and is equipped with a sample stage that can move, linearly and reciprocally, in the horizontal direction while holding the sample and the fluorescent plate as a unit, in the horizontal direction. Further, in this Lang's camera is provided, so-called, a rotation arm being equipped with the X-ray source, including an X-ray tube in a tip portion thereof, for the purpose of enabling θ rotation thereof.

Patent Document 1: U.S. Patent Application Publication No. 2004/0223586 A1;

Patent Document 2: Japanese Patent Laying-Open No. 2004-20397 (2004); and

Patent Document 3: Japanese Patent Laying-Open No. Hei 07-140096 (1995).

BRIEF SUMMARY OF THE INVENTION

As was mentioned above, for the small angle X-ray scattering apparatus, to which the present invention relates, an apparatus of the vertical type is already known, as well as, a normal one of the normal horizontal type, however, in particular, with the small angle X-ray scattering apparatus having such the vertical structure, from such the structures thereof, it is possible to make an analysis upon a liquid-like sample, with using the scattering X-ray formed by irradiating the X-ray that sample, vertically (i.e., transmission diffraction of small angle X-ray), but it is impossible to conduct such the measurement, being so-called a reflection small angle X-ray diffraction or an in-plane small angle X-ray diffraction, mainly applied into an analysis of the crystal and/or the thin film, which are formed on a surface of a glass, a Kapton(®) film or the like, for example.

Also, within the crystal evaluation apparatus, which is known in the Patent Document 2 mentioned above, there is adopted such the structures therein, that the X-ray irradiation means and the X-ray detection means can rotate with respect to the sample holder, however the object thereof is for enabling multilateral detections of the crystals of proteins distributing in the spherical manner, but it is not in such the structures for achieving therewith plural numbers of small angle X-ray scatterings; such as, a transmission small angle X-ray diffraction measurement, a reflection small angle X-ray diffraction measurement, an in-plane small angle X-ray diffraction measurement, etc., for example, which can be achieved by the small angle X-ray scattering apparatus, to which the present invention relates. Further, also the Lang's camera known by the Patent Document 3 mentioned above is not in such the structures for achieving the plural numbers of small angle X-ray scatterings therewith.

Then, according to the present invention by taking the drawbacks or problems of the convention arts mentioned above into the consideration thereof, an object thereof is to provide a small angle X-ray scattering apparatus, for enabling the plural numbers of small angle X-ray scatterings, such as, the transmission small angle X-ray diffraction measurement, the reflection small angle X-ray diffraction measurement, the in-plane small angle X-ray diffraction measurement, etc., upon a sample, corresponding thereto, while fixing that sample, and further a method for measuring the small angle X-ray scattering for the thin film-like sample, which can be achieved by such the apparatus.

For accomplishing the object mentioned above, according to the present invention, first of all, there is provided a vertical/horizontal small angle X-ray scattering apparatus, comprising: an X-ray generating apparatus, which is configured to generate X-ray; an optic system, which is configured to form the X-ray generating from said X-ray generating apparatus into a predetermined incident beam of X-ray; a sample holder portion, which is configured to mount a sample to be measured thereon, to irradiate said incident beam of X-ray upon said sample; a vacuum path, which is configured to pass through small angle X-ray from the sample on said sample holder portion; and an X-ray detector, which is configured to detect the small angle X-ray passing through said vacuum path, wherein said sample holder portion is fixed on a support base, said X-ray generating apparatus, said optic system, said vacuum path and said X-ray detector are attached on a bench, and said bench is rotatable around said sample holder portion, thereby enabling plural numbers of measurements of small angle X-ray scattering.

Also, according to the present invention, within the vertical/horizontal small angle X-ray scattering apparatus, as described in the above, it is preferable that said bench attaching said X-ray generating apparatus, said optic system, said vacuum path and said X-ray detector thereon is rotatable into almost vertical and almost horizontal positions, or that said sample holder portion has a rotation shaft as a unit, and said bench attaching said X-ray generating apparatus, said optic system, said vacuum path and said X-ray detector thereon is rotatable centering around said rotation shaft, and further that said sample holder portion further comprises a mechanism, which is configured to adjust a vertical position of said sample mounted thereon.

Further, according to the present invention, also for accomplishing the object mentioned above, there is also provided a method for measuring small angle X-ray scattering, comprising the following steps of: generating X-ray by an X-ray generating apparatus; forming the X-ray generated from said X-ray generating apparatus into a predetermined incident beam of X-ray through an optic system; irradiating said formed incident beam of X-ray upon a sample mounted on a sample holder portion; and detecting small angle X-ray from said sample by an X-ray detector, wherein upon said sample, which is formed to be a thin film on a surface of a laminar substrate, said incident beam of X-ray is incident from side-end surface thereof, at an incident angle having a negative angle with respect to a surface of said sample formed to be the thin film.

However, according to the present invention, within the method for measuring small angle X-ray scattering, as described in the above, it is preferable that a part of said optic system has a CMF mirror, and it condenses the X-ray generated from said X-ray generating apparatus, and also turns into monochromatic X-ray.

As was mentioned above, with the vertical/horizontal small angle X-ray scattering apparatus, according to the present invention, for various kinds of samples including a liquid sample therein, since it is possible, at least, to irradiate the incident beam of X-ray upon the sample in almost horizontal or vertical direction, while keeping the sample to be mounted and fixed on the sample holder portion, which is fixed, with simple operations of replacement, it is possible to achieve the measurements of the transmission small angle, reflection small angle and the in-plane small angle, for example, by only one (1) set of the apparatus, and it is also possible to execute analysis and/or evaluation, fully, upon various kinds of samples, including soft materials and biomaterials, etc, for example, and further, since the measurements can be made by only one (1) set of the apparatus, then there can be achieved superior effects, i.e., it does not occupying a large space for installation, and it is economical. Also, with the method for measuring the small angle X-ray scattering, according to the present invention, there can be obtained superior effects, i.e., a preferable small angle resolution can be obtained even for the thin film-like sample.

BRIEF DESCRIPTION OF THE DRAWINGS

Those and other objects, features and advantages of the present invention will become more readily apparent from the following detailed description when taken in conjunction with the accompanying drawings wherein.

DESCRIPTION OF THE PREFERRED EMBODIMENTS

Hereinafter, embodiments according to the present invention will be fully explained by referring to the attached drawings.

Figure 1:
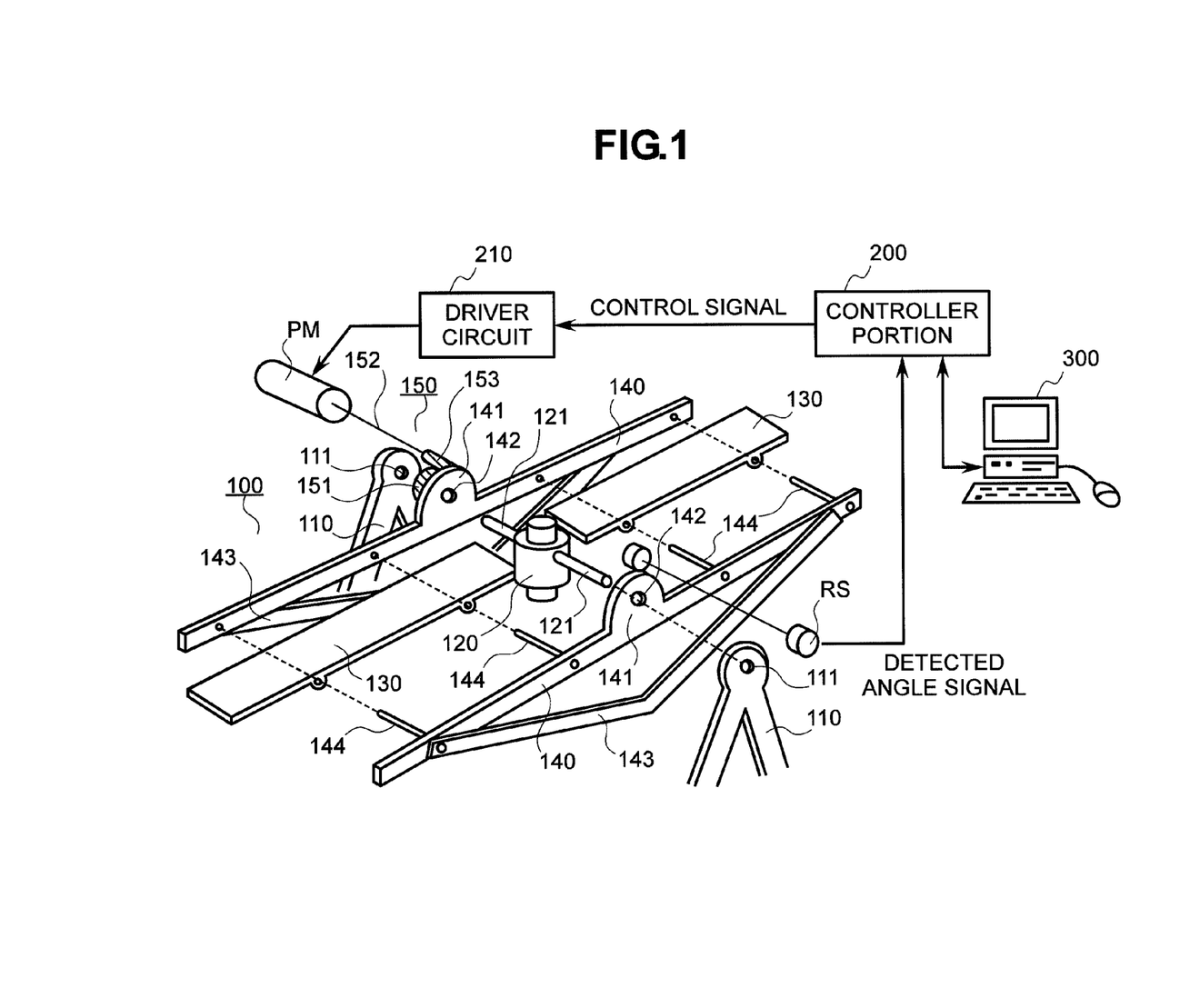
FIG. 1 is an exploded perspective view of a vertical/horizontal small angle X-ray scattering apparatus for showing the entire structures thereof, according to an embodiment of the present invention, and in particular, mainly the structures around a rotatable bench thereof.

First of all, FIG. 1 shows an example of the structures of a small angle X-ray scattering apparatus, mainly, around a fixing base for fixing thereon each of elements, which will be explained below; i.e., so-called a bench 100. This bench 100 has a pair of rotation support bases 110 and 110, each having an outer configuration of being about triangle, and a bottom side of those support bases (not shown in the figure) are disposed/fixed on a floor of a laboratory, or the like, for example. And, in the vicinity of summits of the triangles of those support bases 110 and 110, though will be explained in more details later, there are opened shaft insertion openings 111 and 111, respectively, into which are inserted tips of a pair of rotation shafts 121 and 121 that are formed extending from a sample holder portion 120.

On the other hand, this bench 100 comprises plate-like (i.e., laminar) members 130 and 130, both making up a fixing plate, for fixing thereupon each of optical elements, which buildup the small angle X-ray scattering apparatus, the details thereof will be explained below, and further on both sides of those plate-like members are attached with supporting frames 140 and 140, for mechanically supporting the plate-like members 130 and 130 and also for supporting those to be rotatable. Thus, on each of those supporting frames 140 and 140 is formed a convex portion 141 or 141, being about circular in the shape thereof, at around the center on the side extending into the longitudinal direction thereof, and at a central portion thereof is opened a shaft insertion openings 142 or 142, into which is inserted one of the pair of rotation shafts 121 and 121, being formed extending from the sample holder portion 120 mentioned above. With such the structures, the plate-like members 130 and 130, i.e., a fixing base, are rotatable around the rotation support bases 110 and 110 (a rotation shaft) of the sample holder portion 120 mentioned above, together with supporting frames 140 and 140. Further, reference numerals 143 and 143 in this figure depict beams, which are attached on the supporting frames 140 and 140 for reinforcing the strength thereof, and reference numerals 144, 144 . . . depict fixing members, such as, bolts and nuts or the like, for example, in order to fix the supporting frames 140 and 140 and the plate-like members 130 and 130 as a unit, respectively.

Figure 2:
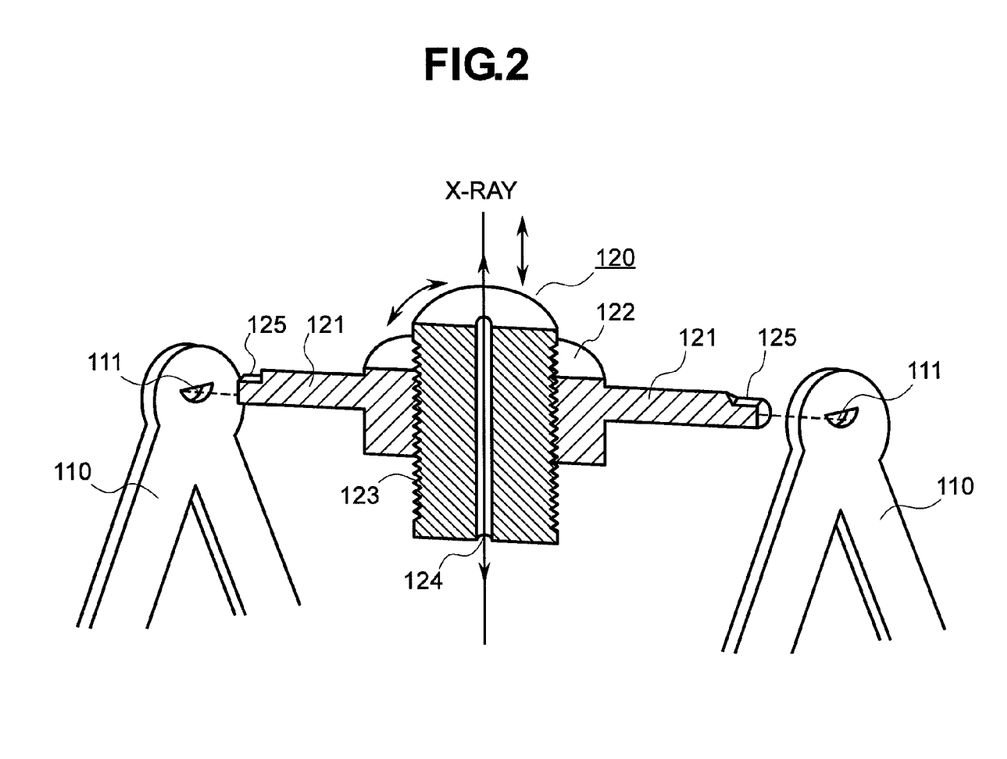
FIG. 2 is a perspective view for showing the details of a sample holding portion within the rotatable bench of the vertical/horizontal small angle X-ray scattering apparatus, including a cross-section of a part thereof.

Next, FIG. 2 attached herewith shows the details of the sample holder portion 120 mentioned above, through a perspective view, including a cross-section of a part thereof. As is apparent from the figure, this sample holder portion 120 is made up with a main body 122 of about disc- or cylinder-like shape and a sample mounting table 123 located at the center thereof, being movable up and down (i.e., vertically) and in a cylindrical shape. Further, from both sides of the main body 122 of disc- or cylinder-like shape, opposing to each other, are formed the pair of rotation shafts 121 and 121 mentioned above, extending as a unit therewith, and on an inner periphery thereof are formed helical grooves. On the other hand, upon an outer peripheral surface of the sample mounting table 123 are also formed the helical grooves, and with this, it is possible to move/adjust the sample mounting table 123 (i.e., a mounting surface on an upper surface thereof), vertically, with respect to the main body 122, by rotating the sample mounting table 123. Also, as is apparent from the figure, a passage opening 124 for X-ray is drilled at the central portion of this sample mounting table 123, i.e., along the rotation axis thereof.

Further, as is apparent from FIG. 2 mentioned above, cutout portions 125 and 125 are formed at the tip portions of the rotation shafts 121 and 121, which are extended from the both opposing surfaces of the main body 122, and therefore, those tip portions can be inserted into shaft insertion holes 111 and 111, which are formed in the vicinity of the summit of the rotation support bases 110 and 110 mentioned above, and thereby enabling to hold the said sample holder portion 120, horizontally, i.e., the sample-holding surface thereof (in more details, the mounting surface on the upper surface of the sample mounting table 123).

Figure 3:
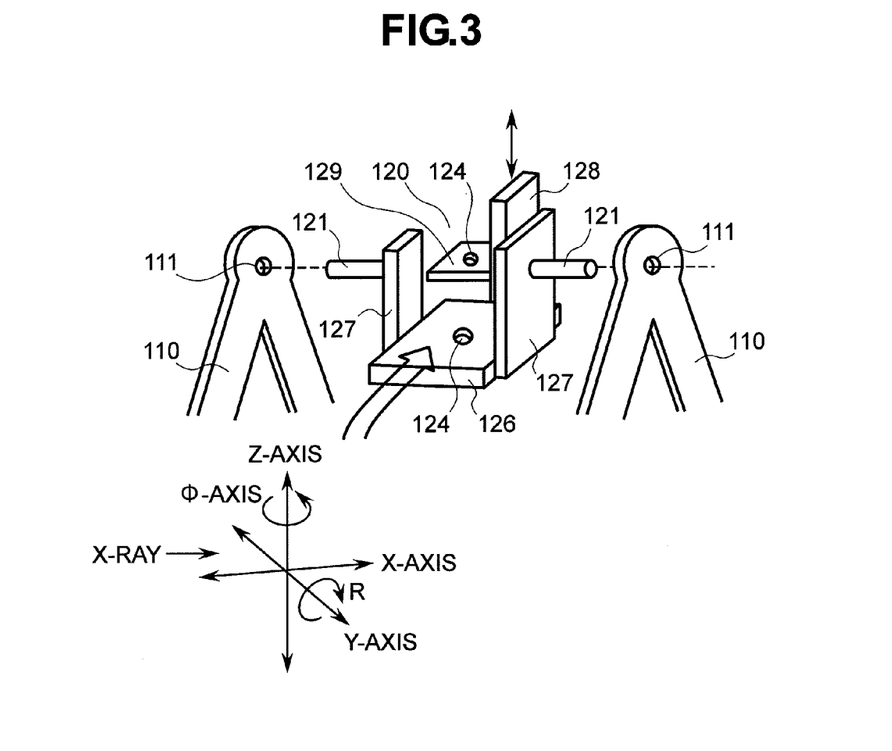
FIG. 3 is a partially enlarged perspective view for showing a variation of the sample holding portion within the vertical/horizontal small angle X-ray scattering apparatus mentioned above.

However, the sample holder portion 120 should not always be restricted to such structures as shown in FIG. 2 mentioned above, but it may be that having such the structures as shown in FIG. 3 attached herewith, for example. Thus, with this sample holder portion 120, as apparent from the figure, arms 127 and 127 are attached on both sides of a lower-side base 126 formed in a rectangular plate-like shape, around the center portion of which is formed the passage opening 124 for X-ray, and on those arms are fixed the above-mentioned rotation shafts 121 and 121 are fixed, respectively. And, on one of the arms 127 (i.e., on the right-hand side in the figure) is attached an up-down stage 128, being about "T"-like in the outer configuration thereof, and this stage 128 has a sample table 129, also being formed with the passage opening 124 for X-ray at about the central portion thereof and is disposed into the horizontal direction. Also, this stage is also movable up and down (i.e., in the vertical direction) with an aid of a sliding groove or the like, for example, which is formed on the arm, though not shown in the figure, and with this, it achieves such the structures that the upper surface of the sample table can be adjusted to be coincident with the axial center of the rotation shafts 121 and 121 mentioned above. Also, upon the upper surface of the lower-side base 126 of the sample holder portion 120 may be disposed a stage, being rotatable or movable with respect to each of axes shown in the figure, and replacing the reflection in-plane measurement and the sample, it is also possible to make the conventional small angle measurement with transmission X-ray.

Herein, turning back to FIG. 1 mentioned above, again, on the rotatable bench 100, the detailed structures of which are explained in the above, there are further attached a rotation mechanism 150 for rotating that bench 100, and a detector portion RS for detecting a rotation angle of that bench 100. However, in this example, as is apparent from FIG. 4 attached herewith, there is further attached a spur gear 151, on an outer surface of the circular convex-like portion 141, which is formed on one of the support frames 140 at about the central portion thereof, and with this spur gear 151 is meshed a worm gear 153, which is attached on a rotation shaft 152 of a pulse motor PM, for example. Thus, such the structures build up the rotation mechanism 150, for enabling automatic change of an angle of the bench 100, through rotational driving by the pulse motor PM.

Figure 4:
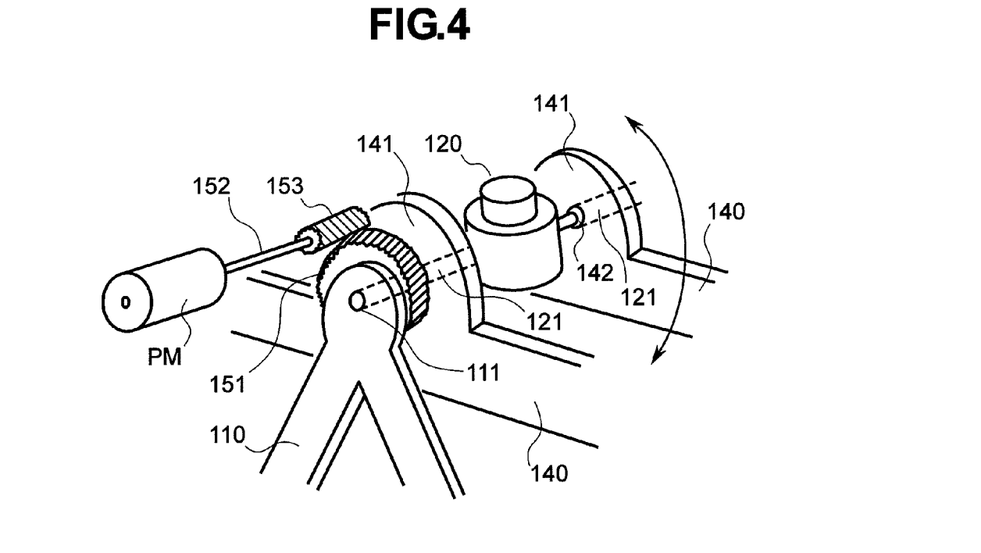
FIG. 4 is a partially enlarged perspective view for showing the detailed structures of a rotation mechanism within the vertical/horizontal small angle X-ray scattering apparatus mentioned above.

On the other hand, for example, the rotation angle sensor RS is attached upon the other circular convex portion 141, and this detects an inclination angle of that movable bench 100. With such the structures, upon a rotation angle signal from that rotation angle sensor RS, a controller portion 200 produces a control signal for controlling the above-mentioned pulse motor PM, and thereby controlling the rotation of the pulse motor PM through a driver circuit 210. And, with inputting a desired inclination angle from a control computer 300 or the like of the apparatus, for example, it is possible to incline that bench 100 by the desired angle, automatically. Or, upon a display of the computer 300, it is also possible to display the inclination angle of the bench 100 detected.

Figure 5:
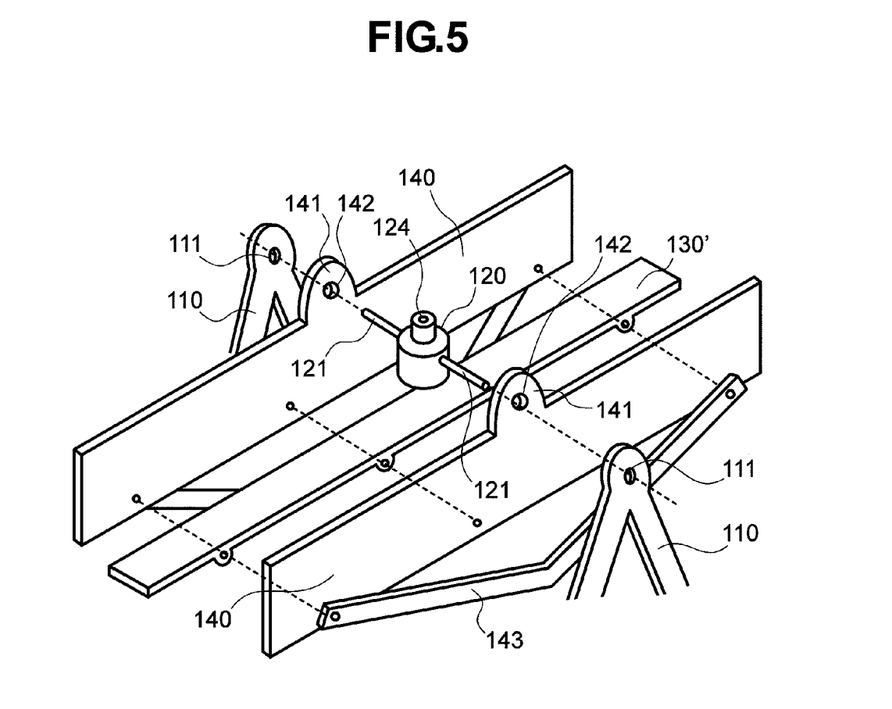
FIG. 5 is an exploded perspective view for showing other variation of the bench within the vertical/horizontal small angle X-ray scattering apparatus mentioned above.

Further, FIG. 5 attached herewith shows a variation of the bench 100, an example of which is shown in FIG. 1 mentioned above. Also, the bench 100 according to this variation has, basically, the structures similar to those shown in FIG. 1 mentioned above. However, as is apparent from the figure, with the structures of this variation, the fixing base for fixing every optical elements building up the small angle X-ray scattering apparatus thereon is made up with one (1) piece of a plate-like member 130'. Further, accompanying with such change, the height of supporting frames 140 and 140 attached on both sides of that plate-like member 130' comes to be large, and with this, the one (1) piece of the plate-like member 130' will not abut or touch on the sample holder portion 120 mentioned above even if the bench 100 rotates.

Figure 6:
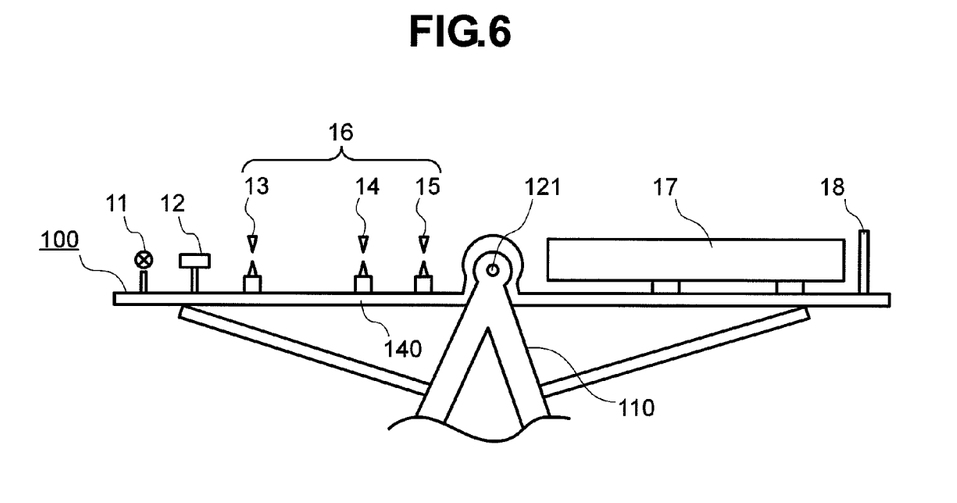
FIG. 6 is a side view for showing every element to be attached on the rotatable bench, for building up the vertical/horizontal small angle X-ray scattering apparatus mentioned above, in particular, under the condition that the bench is set up into the horizontal direction.

Next, FIG. 6 attached herewith shows an outline of the optical elements of the small angle X-ray scattering apparatus, to be attached on the rotatable bench 100, the detailed structures of which are explained in the above, in the form of a block diagram. As is apparent from the figure, on the bench 100 mentioned above are disposed the followings, sequentially from the left-hand side in the figure; i.e., an X-ray generating apparatus 11 including a generating source of X-ray, a CMF mirror 12, and a three (3) slits pin-hole optic system 16, being constructed with a first slit 13, a second slit 14, and a third slit 15, for example. Thus, with this, the X-ray from the X-ray generating apparatus 11 mentioned above can be a desired X-ray incident beam, to be irradiated upon a sample mounted on the sample holder portion 120 mentioned above at a desired incident angle. And, the small angle X-ray scattering from that sample, passing through a vacuum path 17 disposed in coaxial with the X-ray incident beam, reaches to a two-dimensional X-ray detector 18; thereby an analysis is made upon the sample.

Figure 7A:
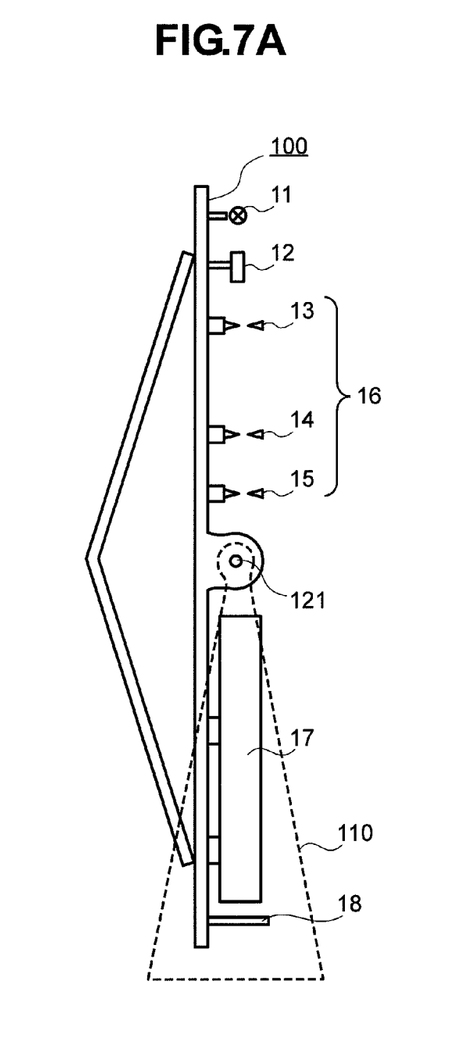
FIGS. 7A and 7B are side views of the vertical/horizontal small angle X-ray scattering apparatus mentioned above, in particular, under the condition that the bench is set up into the vertical direction.
Figure 7B:
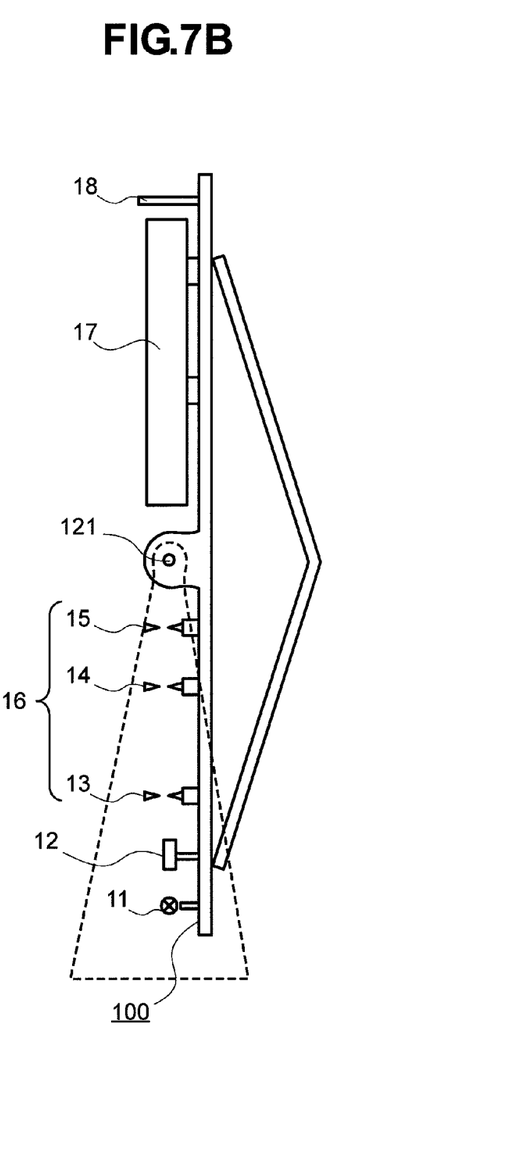

However, in this FIG. 6 is shown the side view of the vertical/horizontal small angle X-ray scattering apparatus according to the present invention, in particular, under the condition of setting that bench 100 laying down, e.g., almost horizontal (0 degree in the inclination angel), but in FIGS. 7A and 7B attached herewith are shown the side views of the apparatus, under the condition of setting that bench 100 standing up, e.g., almost vertical (+90 degree or −90 degree in the inclination angle).

Thus, FIG. 7A shows the condition where the bench 100 is rotated to stand up, almost vertically (+90 degree in the inclination angle), i.e., under the condition where the X-ray generating apparatus 11 is set up to position at an upper part. However, in this figure is shown by broken lines the support base 110, being triangle in the outer configuration thereof. However, the analyzing operation by the small angle scattering of X-ray upon the sample is similar to that shown in FIG. 6 mentioned above, but except that the small angle X-ray scattered upon the sample passes through the passage opening 124 for X-ray, which is opened at the center of the sample mounting table 123 (along the rotation axis thereof) of the sample holder portion 120. Also, FIG. 7B shows the condition where the bench 100 is rotated in the opposite direction to stand up, almost vertically (−90 degree in the inclination angle), i.e., under the condition where the X-ray generating apparatus 11 is set up to position at a lower part. Also, not shown in the figure herein, but it is also possible to attach the above-mentioned X-ray detector 18 on the sliding mechanism, thereby to bring it to be movable in the front and back directions of the X-ray incident beam.

Next, further, explanation will be made on the details of the optical elements for building up the small angle X-ray scattering apparatus, being attached on the upper surface of the plate-like members 130, i.e., the fixing base of the bench 100, the inclination angle of which can be set up to be nearly horizontal (the inclination angle=about 0 degree) or nearly vertical (the inclination angle=about 90 degree), as was mentioned above, by referring to FIG. 8 attached herewith. First of all, the X-ray generating apparatus 11 is constructed such that the X-ray tube 11 is attached on a four-axes stage 11-1 for use of positional adjustment of the X-ray tube 11-2, which can be moved or adjusted into X-axis direction (right and left), Y-axis direction (front and back), Z-axis direction (up and down), and θ-axis direction (rotation around the X-ray source in the horizontal direction), through manual operations. The CMF mirror 12 is also attached on a CMF mirror fixing support 12-1 having a mechanism for adjusting an inclination between the X-ray and the horizontal direction. Also, the first slit 13, the second slit 14 and the third slit 15 are disposed within vacuum slit boxes 13-2, 14-2 and 15-2, respectively, which are attached on the slit fixing supports 13-1, 14-1 and 15-1, each having adjusting mechanisms in the Y-axis direction (front and back) and the Z-axis direction (up and down), and further between those boxes are attached tubes 16-1 for defining the vacuum path therein. Thus, with this, there is defined the vacuum path of the X-ray incident side.

Figure 8:
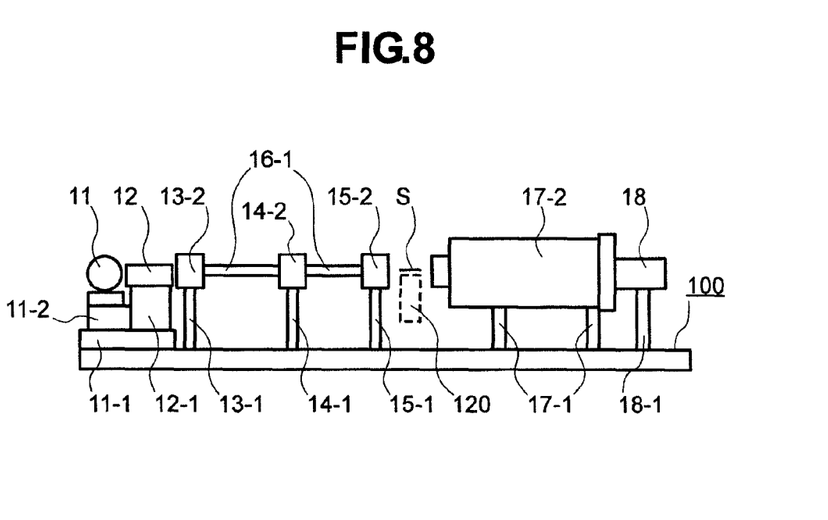
FIG. 8 is a side view for showing the detailed structures of optical elements to be disposed on the bench, building up the vertical/horizontal small angle X-ray scattering apparatus mentioned above.

On the other hand, also the above-mentioned vacuum path 17 of the detector side is fixed on the fixing support 17-1, and on the exit side thereof (i.e., on the right-hand side in the figure) is attached the two-dimensional X-ray detector 18 mentioned above, through a direct beam stopper box 17-2. Further, this detector 18 is also attached on a fixing support 18-1, in the similar manner.

Following to the above, hereinafter, detailed explanation will be made on the measuring method with using the vertical/horizontal small angle X-ray scattering apparatus, according to the present invention, the structures of which was explained in the above.

(1) Measurement by Transmission Small Angle

Figure 9A:
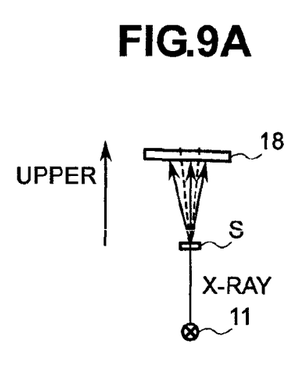
FIGS. 9A to 9C are views for explaining the principle for conducting a measurement upon a transmission small angle, with the vertical/horizontal small angle X-ray scattering apparatus mentioned above.
Figure 9B:
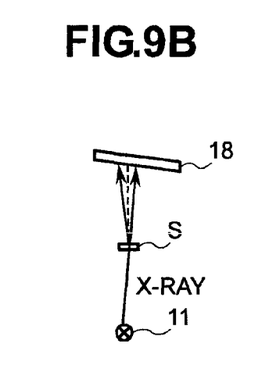
Figure 9C:
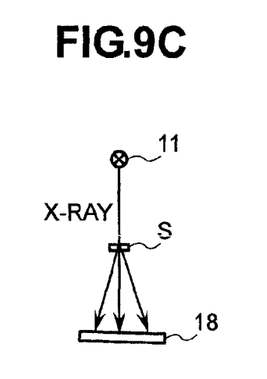

This is a method for measuring the small angle X-ray scattering from the sample S, while setting up the vertical/horizontal small angle X-ray scattering apparatus to be vertical, as shown in FIGS. 9A to 9C; i.e., setting the bench 100 at the inclination angle=about 90 degree (see FIGS. 7A and 7B mentioned above). This is effective, in particular, for a liquid sample, and measurement is made upon the small angle X-ray scattering from the sample while irradiating the X-ray from an upper portion of the sample S.

Further, FIG. 9A shows the measuring method with a transmission method with a normal small angle, and also FIGS. 9B and 9C show the measurement method, being available with applying the vertical/horizontal small angle X-ray scattering apparatus according to the present invention therein. First of all, in the measurement of the small angle of transmission, a diffracted X-ray can be observed in a small angle region when distance between films (i.e., the thickness thereof) is large (this is due to the fact that there is a film inclining only by an angle θ, which will be mentioned below, within relatively thick films), however, on the thin film produced with an accuracy of film thickness of an atom level, no diffraction peak can be observed when irradiating the X-ray perpendicular to the sample S. Then, for observing this diffraction peak, applying such the mechanism for changing an incident angle, according to the present invention, enables the X-ray being incident upon, at an angle satisfying a normal line of diffraction surface of the sample.

For example, assuming that the distance (the thickness) of the film is "d" (nm) and wavelength of the incident X-ray is "λ" (nm), then the diffraction angle "θ" can be calculated from Bragg's equation, as follows:

$$2d \sin \theta = \lambda$$

Where, "θ" is a half (½) of an angle defined between the incident X-ray and the diffracted X-ray. In more details, as shown in FIG. 9B, in particular, the above-mentioned bench 100 is set up to be vertical (i.e., the inclination angle=about +90 degree), and further the inclination angle thereof is also changed, approximately 0 to ±3 degree, for example, depending on necessity thereof, with using the mechanism for changing the incident angle, according to the present invention, and thereby it is possible achieve an effective measurement on the sample mentioned above, such as, the thin-films on the substrate, or the like, for example.

(2) Measurement by Reflection Small Angle

Figure 10:
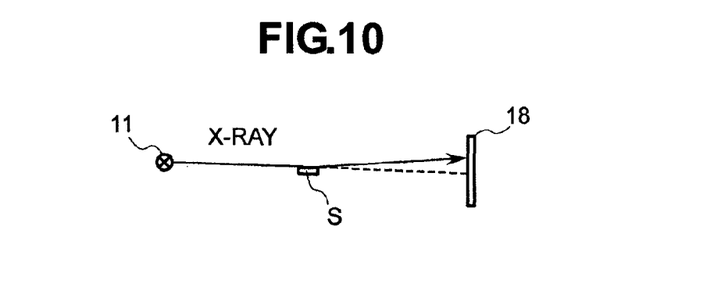
FIG. 10 is a view for explaining the principle for conducting a measurement upon a reflection small angle, with the vertical/horizontal small angle X-ray scattering apparatus mentioned above.

As shown in FIG. 10, this is a method wherein the vertical/horizontal small angle X-ray scattering apparatus is almost horizontal, i.e., setting up the bench 100 to be about horizontal (see FIG. 6 mentioned above), and the X-ray beam is irradiated upon the sample, by a very small incident angle (the inclination angle: 0 to ±3 degree), thereby to detect the position of the small angle X-ray reflected, this is the measuring method being effective, in particular, for analyzing of the thin-film sample on the substrate, etc. However, with this measuring method, by adjusting the sample-mounting table 123, which is movable up and down on the sample holder portion 120, it is possible to bring the surface position of the sample S to be equal to the height of the X-ray beam.

(3) Measurement by Reflection In-plane Small Angle

Figure 11A:
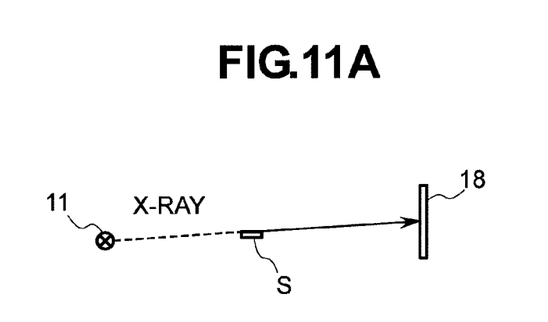
FIGS. 11A and 11B are views for explaining the principle for conducting a measurement upon an in-plane small angle, with the vertical/horizontal small angle X-ray scattering apparatus mentioned above.
Figure 11B:
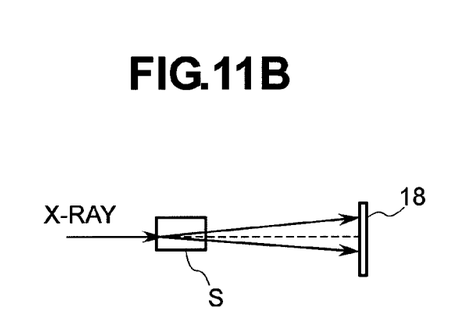

As shown in FIGS. 11A and 11B, this is a method wherein the vertical/horizontal small angle X-ray scattering apparatus is almost horizontal, i.e., setting up the bench 100 to be about horizontal (see FIG. 6 mentioned above), and the X-ray beam is irradiated upon the sample, by a very small incident angle (the inclination angle: 0 to ±3 degree), thereby to detect the position of the small angle X-ray reflected, and this is also effective for analyzing of the thin-film sample on the substrate, etc. In particular, this is effective for small angle measurement on the thin film, for example, having 2θ=0.5 degree or less than that (q=4π sin θ/λ=0.356 nm), which cannot be measured by the reflection small angle of (2) mentioned above. Further, with this measuring method, by adjusting the sample-mounting table 123, which is movable up and down on the sample holder portion 120, it is possible to bring the surface position of the sample S to be equal to the height of the X-ray beam. Moreover, herein FIG. 11A is the side view and FIG. 11B is an upper view thereof.

Further, here will be given explanation on a method for measuring the small angle X-ray scattering for the thin film-like sample, according to the present invention, which can be achieved by applying the vertical/horizontal small angle X-ray scattering apparatus mentioned above, in more details thereof, hereinafter.

As was mentioned above, the method for measuring the small angle X-ray scattering on the thin-film sample is already known (for example, "Characterization of Polymer Thin Films with Small-Angle X-ray Scattering under Grazing Incidence (GISAXS)", SYNCHROTRON RADIATION NEWS, Vol. 15, No. 5, 2002, pp 35-42). However, with such method, since measurement is made on the reflection small angle of incident X-ray, basically, then the path of the X-ray passing within the sample comes to be long, in particular, when the incident angle is equal to 0.4° or smaller than that, and therefore, there is a possibility that the measurement cannot be made due to the weak X-ray scattered/reflected within the sample. Regarding this, explanation will be made, by referring to FIGS. 15A and 15B, hereinafter.

Figure 15A:
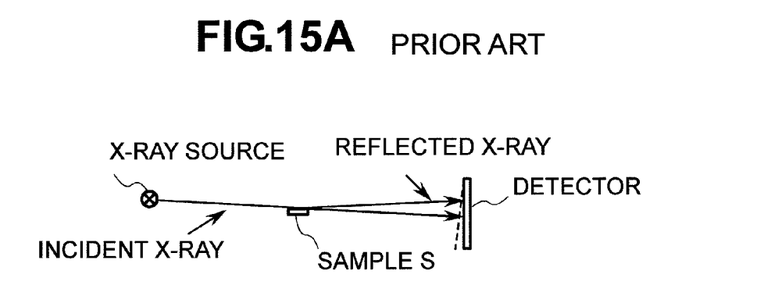
FIGS. 15A to 15C are views for explaining the drawbacks within the conventional method for measuring the small angle X-ray scattering.
Figure 15B:
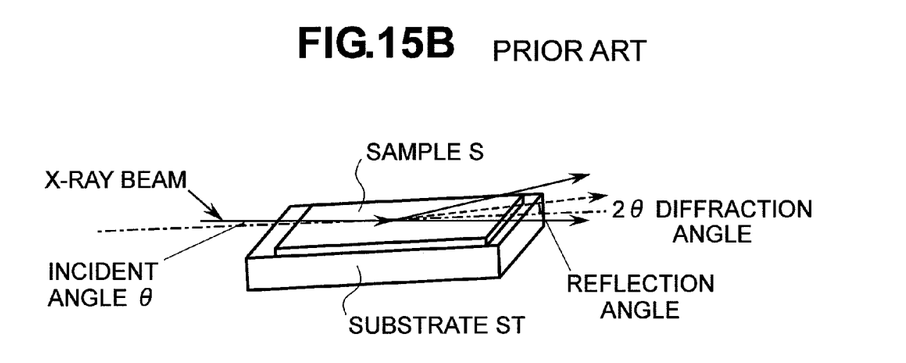
Figure 15C:
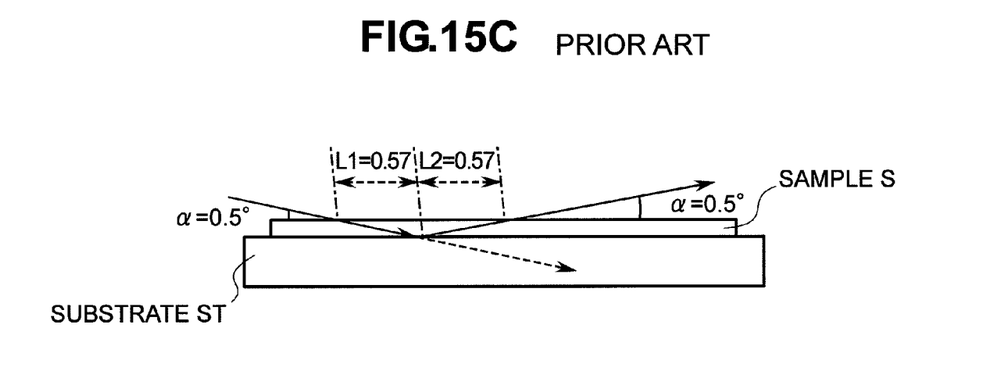

However, within an example shown in those figures, the thin film-like sample S is formed on the surface of the plate-like substrate ST, and if putting the incident angle to be "α", then the path "L1" on the incident side and the path "L2" on the reflection side are as follows. Where, thickness of the sample is t=1 μm=0.001 mm, and there is used CuKα X-ray.

$$L1=L2=t/\sin \alpha \text{(mm)}$$

For example, in case where the incident angle mentioned above is 0.5°, L1=L2=0.001/sin 0.5°=0.11 (mm). Further, this value is about one tenth (1/10) of an optimal thickness of the polymeric material, which the CuKα X-ray can pass through (approximately 1 mm). Thus, when the incident angle "α" is large, although the distance is short, through which the scattered radiation generated within the sample S passes within the sample S, but on the other hand, when this incident angle "α" is small, the distance comes to be long, through which the scattered radiation pass within the sample S, and as a result thereof measurement cannot be made thereupon.

Furthermore, by taking the scattering volume from the sample into the consideration, it is enough to make the incident angle "α" small, but the total reflection of the incident X-ray becomes large upon the sample surface, and further a volume of the scattered radiation becomes large, which is absorbed within the sample; i.e., an intensity of scattering is lowered in the direction of the in-plane. On the other hand, enlarging this incident angle "α" reduces the scattering volume of sample, and results in a reason of weakening the intensity of scattering. Accordingly, with results of various experiments made by the inventors so on, it is found that there is a limitation with the measuring method of the small angle X-ray scattering mentioned above, and in particular, it is impossible to make measurement when 2θ=0.4° or lower than that.

Figure 12A:
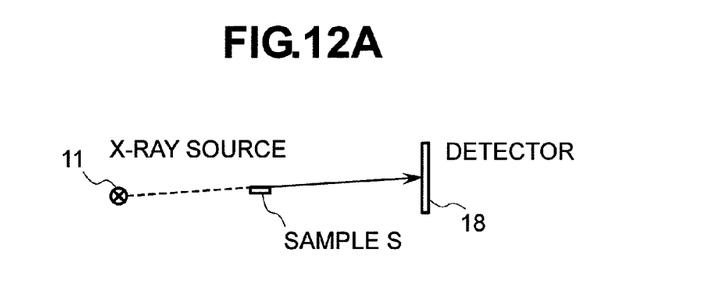
FIGS. 12A to 12C are views for explaining the principle of a method for measuring the small X-ray scattering, according to the present invention.
Figure 12B:
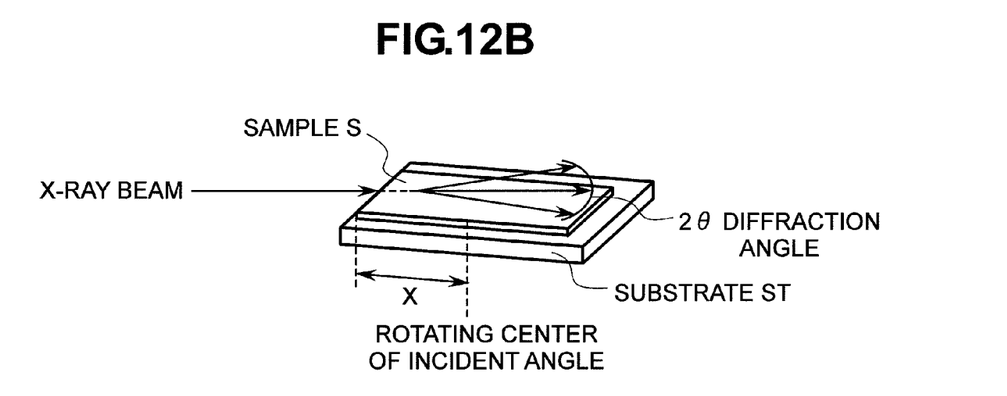
Figure 12C:
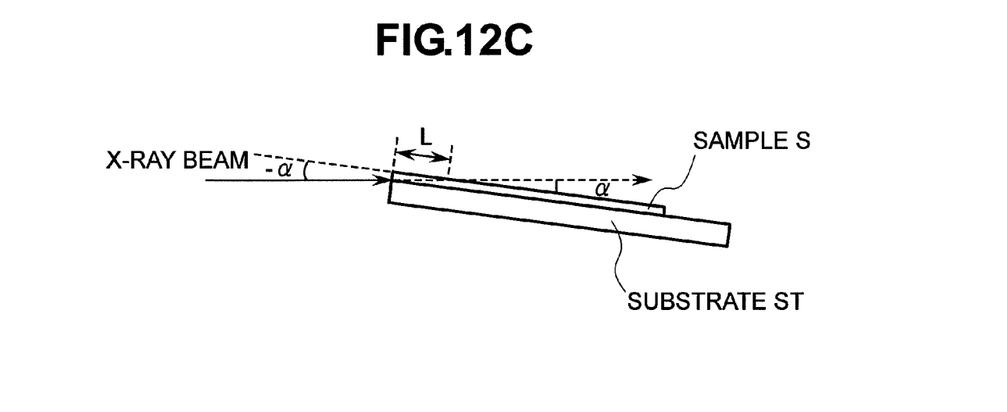

Then, according to the present invention, as was shown in FIGS. 11A and 11B mentioned above, and further, as will be shown in FIGS. 12A to 12C below, there is proposed a measuring method of the small angle X-ray scattering, wherein the X-ray to be irradiated on the thin film-like sample S is incident upon the surface thereof, at the incident angle having a negative value (−α). Further, with this, as is apparent from FIGS. 13A to 13C; the X-ray is irradiated from the side-end surface of the thin film-like sample S. As a result thereof, the distance L, though which the incident X-ray passes within the sample S, can be obtained, easily, as follows, only by the thickness "t" of the sample and the incident angle (−α) mentioned above.

$$L=t/\sin \alpha$$

For this reason, it is possible to determine the transmission distance L, easily, satisfying μ·L where the scattering intensity is strongest (herein, "μ" is coefficient of the X-ray absorption of the film material). In other words, it is possible to determined the incident angle (−α), easily, by the optimal transmission distance "L" and the film thickness "t".

However, as is apparent from the figures mentioned above, with the measuring method of the small angle X-ray scattering, according to the present invention, differing from the conventional measuring method of the small angle X-ray scattering, a preferable small angle dissolution can be obtained, without accompanying the reflection upon the surface of the substrate ST, on the upper surface of which is formed the thin film-like sample S, and further without receiving ill influences due to the total reflection caused when setting the incident angle to be small. For example, as will be mentioned below, the measurement can be made at 2θ=0.4° lower than that (but, down to 2θ=0.1°), which is impossible with the conventional measuring method.

Example 1

Calculation of the Incident Angle

Thickness of sample: t=0.001 mm
Transmission distance: L=1 mm
Incident angle: $\alpha=\sin^{-1}(t/L)=0.57°$ Further, with the measuring method of the small angle X-ray scattering according to the present invention, which was mentioned in details in the above, as was mentioned above, although the X-ray is irradiated upon the side-end surface of the thin film-like sample S, but in that case, there is necessity of obtaining the incident X-ray being strong in the intensity thereof and also thin, in particular, in the vicinity of that sample. Then, hereinafter, detailed explanation will be made on an optic system for obtaining such the incident X-ray, by referring to FIGS. 13A and 13B.

Figure 13A:
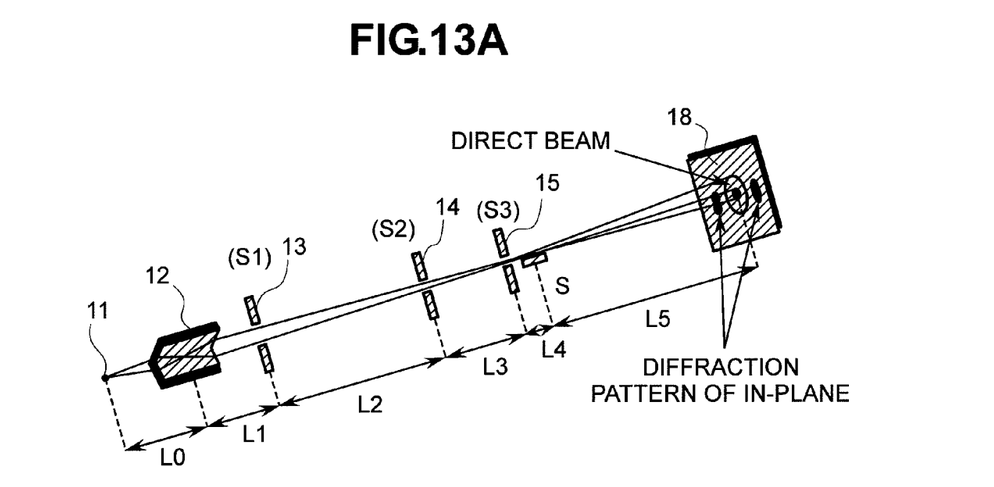
FIGS. 13A and 13B are views for showing an example of an optic system, which is suitable to the method for measuring the small X-ray scattering, according to the present invention.
Figure 13B:
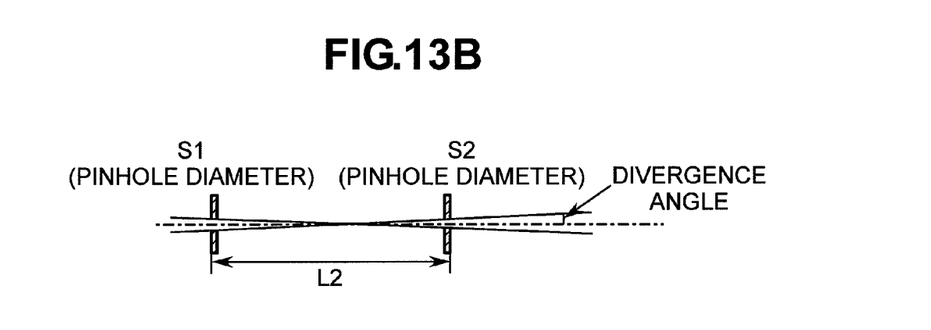

First of all, FIG. 13A shows the entire structures of a small angle X-ray scattering apparatus, applying an X-ray optical element of an artificial multi-layers having graded surface distances, i.e., so-called CMF mirror 12 therein, mainly around that optic system. Thus, within this optic system, diverging X-rays generated from the X-ray source 11 is condensed through the CMF mirror 12 mentioned above, to be monochromatic X-ray. Further, this CMF mirror is a combined or complex monochrometer, being constructed with two (2) pieces of X-ray mirrors of multi-layers (artificial multi-layers), which are disposed perpendicular to each other while abutting the side edges thereof, as is disclosed in U.S. Pat. No. 6,249,566 and Japanese Patent Laying-Open No. 2001-356197 (2001), for example, and it is disposed inclining at a predetermined angle (for example, Confocal Max-Flux of Osmic Inc., of US). Further, the incident X-ray is further thinned by means of the three (3) pieces of slits 13, 14 and 15 (see FIG. 6), and this enables to obtain the optimal small resolution, selectively. Further, FIG. 13B shows an example of an angle of divergence of the incident X-ray, in particular, which can be obtained by the slits S1 and S2, and with this, the angle of divergence can be obtained as below:

$$\text{angle of divergence} = \tan^{-1}\{(S1+S2)/(2 \times L2)\}$$

Where, "S1" indicates a pin-hole diameter of the first slit 13, "S2" a pin-hole diameter of the second slit 14, and "L2" the distance between the first slit 13 and the second slit 14, respectively.

Example 2

For example, in case where L2=470 mm, S1=0.2 mm, and S2=0.1 mm, the angle of divergence obtained is approximately 0.02°.

Thus, with the measuring method of the small angle X-ray scattering, according to the present invention, in particular, with applying the CMF mirror 200, i.e., a crystal monochrometer, since it is possible to obtain the incident X-ray, being strong in the intensity and also thin, in the vicinity of that sample, therefore it is possible to make preferable measurement, in particular, upon the thin film-like sample with using the small angle X-ray scattering.

Figure 14:
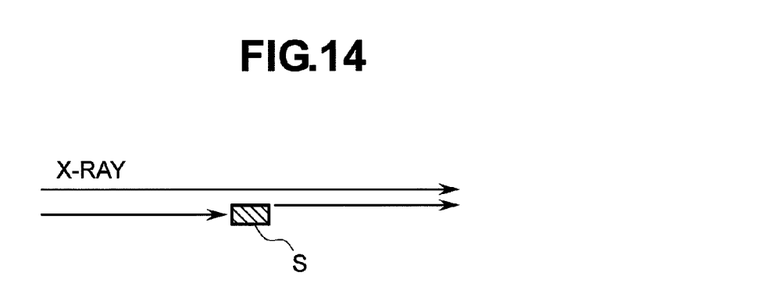
FIG. 14 is a view for explaining the principle for conducting an adjustment (e.g., half position) within the vertical/horizontal small angle X-ray scattering apparatus mentioned above.

In addition to the various kinds of measuring method mentioned above, according to the above-mentioned vertical/horizontal small angle X-ray scattering apparatus, it can be also applied into an adjusting method as shown in FIG. 14, for example. Thus, it is possible to adjust the position of the sample S in the vertical direction (i.e., up and down), so that the X-ray beam is in the half position, when conducting the measurement by the reflection small angle of (2) and/or the measurement by the in-plane small angle of (3) mentioned above, and herein, this half position means such the position that, the intensity of that incident X-ray beam (i.e., an output of the detector) comes to be half (½). With the vertical/horizontal small angle X-ray scattering apparatus mentioned above, the sample can be set at the half position, by adjusting the sample-mounting table 123 mentioned above, which is movable up and down, while changing the bench 100 to be horizontal, i.e., setting it in parallel with the surface of the sample S (see FIG. 6 mentioned above), for irradiating the incident X-ray beam thereupon.

As was fully mentioned above, with the vertical/horizontal small angle X-ray scattering apparatus according to the present invention, since the optical system can be adjusted into the horizontal and vertical directions, freely, it is possible to implement the transmission small angle measurement, the reflection measurement, and the in-plane measurement, which cannot be accomplished without attaching the sample again (i.e., replacing) from the horizontal to the vertical, with easy operations, without accompanying such the replacement of the sample. Also, in particular, when measuring the liquid sample, the measuring system can be rotated around the sample, while keeping the sample to be fixed, i.e., the liquid sample keeps to be held on the sample mounting table, it is possible to make measurement on the sample while changing the incident angle of the X-ray thereupon, preferably. Further, it is also possible to adjust the optic system to be horizontal, and therefore adjustment of the optic system can be made easily. In addition thereto, in particular, for the thin film-like sample S, since the X-ray can be incident upon from the side-end surface thereof; therefore, a preferable small angle resolution can be achieved even for such the thin film-like sample.

EXPLANATION OF NUMERALS

11 - - - X-ray generating apparatus
12 - - - CMF mirror
13 - - - First slit
14 - - - Second slit
15 - - - Third slit
16 - - - Three (3) slits pin-hole optic system
17 - - - Vacuum path
18 - - - X-ray detector
100 - - - Bench
110 - - - Rotation support base
111 - - - Shaft insertion opening
120 - - - Sample holder portion
121 - - - Rotation shaft
122 - - - Main body
123 - - - Sample mounting table
124 - - - Passage opening for X-ray
125 - - - Cutout portion
130 - - - Plate-like member
140 - - - Supporting frame
141 - - - Circular convex-like portion 142 - - - Shaft inserting opening
S - - - Sample While we have shown and described several embodiments in accordance with our invention, it should be understood that disclosed embodiments are susceptible of changes and modifications without departing from the scope of the invention. Therefore, we do not intend to be bound by the details shown and described herein but intend to cover all such changes and modifications that fall within the ambit of the appended claims.

What is claimed is:

1. A vertical/horizontal small angle X-ray scattering apparatus, comprising:
    an X-ray generating apparatus, which is configured to generate X-ray;
    an optic system, which is configured to form the x-ray generated from said X-ray generating apparatus into a predetermined incident beam of X-ray;
    a sample holder portion, which is configured to mount a sample to be measured thereon, to irradiate said incident beam of X-ray upon said sample;
    a vacuum path, which is configured to pass through small angle scattered X-ray from the sample on said sample holder portion;
    an X-ray detector, which is configured to detect the small angle scattered X-ray passing through said vacuum path;
    a support base; and
    a bench,
    wherein said sample holder portion is fixed on said support base, said X-ray generating apparatus, said optic system, said vacuum path and said X-ray detector are attached on said bench, and said bench is rotatable around said sample holder portion, thereby enabling plural numbers of measurements of small angle X-ray scattering.

2. The vertical/horizontal small angle X-ray scattering apparatus, as described in the claim 1, wherein said bench attaching said X-ray generating apparatus, said optic system, said vacuum path and said X-ray detector thereon is rotatable into almost vertical and almost horizontal positions.

3. The vertical/horizontal small angle X-ray scattering apparatus, as described in the claim 1, wherein said sample holder portion has a rotation shaft as a unit, and said bench attaching said X-ray generating apparatus, said optic system, said vacuum path and said X-ray detector thereon is rotatable centering around said rotation shaft.

4. The vertical/horizontal small angle X-ray scattering apparatus, as described in the claim 3, wherein said sample holder portion further comprises a mechanism, which is configured to adjust a vertical position of said sample mounted thereon.

5. A method for measuring small angle X-ray scattering, comprising the following steps of:
    generating X-ray by an X-ray generating apparatus;
    forming the x-ray generated from said X-ray generating apparatus into a predetermined incident beam of X-ray through an optic system;
    irradiating said formed incident beam of X-ray upon a sample mounted on a sample holder portion; and
    detecting small angle scattered X-ray from said sample by an X-ray detector, wherein
    upon said sample, which is formed to be a thin film on a surface of a laminar substrate, said incident beam of X-ray is incident from side-end surface thereof, at an incident angle having a negative angle with respect to a surface of said sample formed to be the thin film.

6. The method for measuring small angle X-ray scattering, as described in the claim 5, wherein a part of said optic system has a CMF mirror, and it condenses the X-ray generated from said X-ray generating apparatus, and also turns into monochromatic X-ray.

\* \* \* \* \*